United States Patent [19]

Fauran et al.

[11] 4,041,030
[45] Aug. 9, 1977

[54] ARYLAMINO PYRIMIDINIC DERIVATIVES

[75] Inventors: Claude P. Fauran, Paris; Guy R. Bourgery, Colombes; Guy M. Raynaud, Paris; Claude J. Gouret, Meudon, all of France

[73] Assignee: Delalande S.A., Courbevoie, France

[21] Appl. No.: 714,473

[22] Filed: Aug. 16, 1976

Related U.S. Application Data

[63] Continuation-in-part of Ser. No. 502,285, Sept. 3, 1974, Pat. No. 3,978,055.

[30] Foreign Application Priority Data

Sept. 20, 1973 France .............................. 73.338310
Mar. 26, 1974 France .............................. 74.10327
July 7, 1976 France .............................. 76.20775

[51] Int. Cl.$^2$ .......................................... C07D 413/12
[52] U.S. Cl. .............................. 544/117; 260/256.4 N; 424/248.56; 424/251; 544/122
[58] Field of Search ................... 260/247.5 D, 256.4 N

[56] References Cited
PUBLICATIONS

Fauran et al., "Chem. Abstracts", vol. 83 (1975) No. 43373e.

Primary Examiner—Henry R. Jiles
Assistant Examiner—R. W. Ramsuer
Attorney, Agent, or Firm—Blanchard, Flynn, Thiel, Boutell & Tanis

[57] ABSTRACT

Compounds of the formula

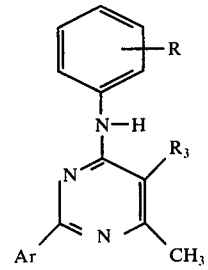

wherein Ar is phenyl or phenyl substituted by one or more halogens, a trifluoromethyl, a methylenedioxy, one or more methoxy, an alkyl having one to 4 carbon atoms or a dimethylamino, and R is

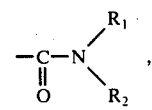

wherein $R_1$ and $R_2$ each are hydrogen or alkyl of 1 to 4 carbon atoms, or

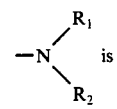

pyrrolidino, morpholino, piperidino or piperazino N'-substituted by alkyl of 1 to 4 carbon atoms, or phenyl, or R is para-2-morpholino ethylamino carbonyl, and $R_3$ is hydrogen or methyl.

The compounds are obtained by reacting 2-Ar-2-chloro-6-methyl pyrimidine, with

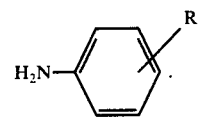

The compounds possess sedative, antiulcerous, antibronchoconstrictive, anticholinergic, diuretic, analgesic myorelaxant and antianoximia properties.

13 Claims, No Drawings

ARYLAMINO PYRIMIDINIC DERIVATIVES

Cross Reference to Related Application

This application is a continuation-in-part of Ser. No. 502,285, filed Sept. 3, 1974 now U.S. Pat. No. 3,978,055, the entire contents of which are incorporated herein by reference.

This invention relates to arylamino pyrimidine compounds. The invention provides compounds having the formula

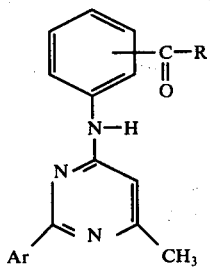

(I)

in which
a. Ar is p-chlorophenyl and R is morpholino or piperidino, or
b. Ar is o-chlorophenyl and R is morpholino, or
c. Ar is m-fluorophenyl and R is piperidino, or
d. Ar is 3,4-methylenedioxyphenyl and R is morpholino or amino, or
e. Ar is 3,4,5-trimethoxyphenyl and R is morpholino or amino.

The invention also provides compounds having the formula

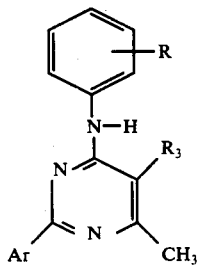

(II)

in which Ar is phenyl or phenyl substituted by a halogen, R is morpholinocarbonyl having the formula

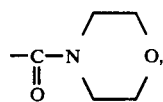

or 2-morpholino ethylaminocarbonyl having the formula

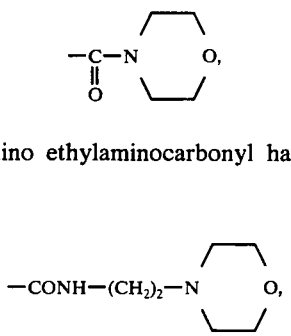

and $R_3$ is hydrogen or methyl.

The process for preparing the compounds according to the invention consists in condensing in acetic acid and in the presence of hydrochloric acid, a 2-aryl-4-chloro-6-methyl pyrimidine of the formula:

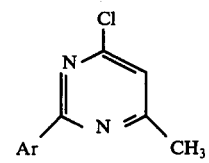

(III)

in which:
—Ar is as defined above, with an anilino derivative of the formula:

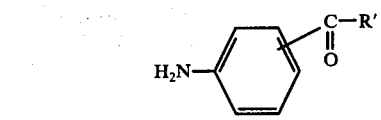

(IV)

in which R' is R as defined above, to produce the compounds of the invention having Formula I. In the case of the compound of Formula II, R' is morpholino. In the case of the compound of Formula II, R' is ethoxycarbonly, and the Formula IV compound is then reacted with 2-morpholino ethylamine to give the Formula II compound.

The following preparations are given by way of example to illustrate the invention.

EXAMPLE 1

2- (3', 4', 5' -trimethoxy phenyl) -4-(para morpholino carbonyl phenylamino) -6-pyrimidine.

Code No.: 72 536

A mixture of 44.2 g of 2-(3', 4', 5' -trimethoxy phenyl)- 4-chloro-6-methyl pyrimidine and 28.6 g of 4-pyrrolidino carbonyl aniline in 300 ccs of acetic acid in the presence of 0.45 cc of concentrated hydrochloric acid is heated at 80° C for 40 minutes. After cooling, the solution is diluted with 2.5 l of water and alkalinized with ammonia.

The precipitate formed is filtered, washed with water and recrystallized from ethyl acetate.

Melting point = 206° C
Yield = 72%
Empirical formula = $C_{25}H_{28}N_4O_5$

| Elementary analysis: | C | H | N |
|---|---|---|---|
| Calculated % | 64.64 | 6.08 | 12.06 |
| Found % | 64.50 | 6.15 | 11.98 |

EXAMPLE :

4-(para 2-morpholino ethylaminocarbonyl) anilino-6-methyl-2-phenyl-pyrimidine

Code No.: 75 0262

1st step: 4-carbethoxy anilino-6-methyl 2-phenyl pyrimidine.

Code No.: 75 0076

A solution of 20.4 g (0.1 mole) of 2-phenyl-4-chloro-6-methyl pyrimidine, 16.5 g (0.1 mole) of 4-amino ethyl benzoate and 0.2 ml of concentrated hydrochloric acid in 200 ml of acetic acid are brought to 90° C and maintained for 1 hour. The resultant solution is diluted with 2.5 liters of water, alkalized with concentrated ammonia, filtered and recrystallized in water.

Melting point = 156° C
Yield = 60%
Empirical formula = $C_{20}H_{19}N_3O_2$

| Elementary analysis: | C | H | N |
|---|---|---|---|
| Calculated (%) | 72.05 | 5.74 | 12.61 |
| Obtained (%) | 71.76 | 5.94 | 12.92 |

2nd step: 4-(para 2-morpholino ethylaminocarbonyl) anilino-6-methyl-2phenyl-pyrimidine.
Code No.: 75 0262

1.6 g of sodium are dissolved in 150 ml of ethanol. To this solution are added 18.2 g (0.14 mole) of 2-morpholino ethylamine and 23 g (0.069 mole) of 4-p-carbethoxy anilino 6-methyl 2-phenyl pyrimidine obtained in the preceding step, The resulting solution is brought to reflux and maintained for seven hours and evaporated, the oil obtained is crystallized in ether, purified by chromatography on a silica gel column (elution agent : chloroform (100%) to chloroform/methanol (50/50) and recrystallized in ethanol.

Melting point = 185° C
Yield = 17%
Empirical formula = $C_{24}H_{27}N_5O_2$

| Elementary analysis: | C | H | N |
|---|---|---|---|
| Calculated (%) | 69.04 | 6.52 | 16.78 |
| Obtained (%) | 68.74 | 6.45 | 16.75 |

The derivatives listed in the following Tables I and II have been prepared by the same modes of operation.

Table 1

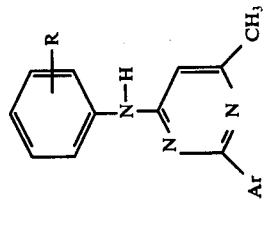

| Code No. | R | Ar | Empirical formula | Molecular weight | Melting point (° C) | Yield (%) | | Elementary analysis | | |
|---|---|---|---|---|---|---|---|---|---|---|
| | | | | | | | | C (%) | H (%) | N (%) |
| 72 256 | (phenyl) | 4-Cl-C₆H₄ | C₂₂H₂₁ClN₄O₂ | 408.38 | 220 | 50 | Calculated<br>Found | 64.62<br>64.51 | 5.18<br>4.98 | 13.70<br>13.51 |
| 72 276 | 4-CH₃-C₆H₄-C(=O)-N(morpholino) | " | C₂₃H₂₃ClN₄O | 406.90 | 238 | 38 | Calculated<br>Found | 7.89<br>7.89 | 5.70<br>5.90 | 13.77<br>13.61 |
| 72 741 | 4-CH₃-C₆H₄-C(=O)-N(piperidino) | 3-F-C₆H₄ | C₂₃H₂₃FN₄O | 390.45 | 214 | 66 | Calculated<br>Found | 70.75<br>70.55 | 5.94<br>5.90 | 14.35<br>14.38 |
| 72 621 | 4-CH₃-C₆H₄-C(=O)-N(piperidino) | 3,4-methylenedioxyphenyl | C₂₃H₂₂N₄O₄ | 418.44 | 260 | 31 | Calculated<br>Found | 66.01<br>65.97 | 5.30<br>5.35 | 13.39<br>13.22 |
| 72 608 | 2-CH₃-C₆H₄-C(=O)-NH₂ | " | C₁₉H₁₆N₄O₃ | 348.35 | 210 | 51 | Calculated<br>Found | 65.51<br>65.43 | 4.63<br>4.69 | 16.08<br>16.03 |

Table 1-continued

| Code No. | Ar | Empirical formula | Molecular weight | Melting point (°C) | Yield (%) | | Elementary analysis | | |
|---|---|---|---|---|---|---|---|---|---|
| | | | | | | | C (%) | H (%) | N |
| 72 536 | 3,4,5-trimethoxyphenyl (H₃CO-, OCH₃, OCH₃) with p-tolyl-morpholinocarbonyl R group | C₂₅H₂₈N₄O₅ | 464.51 | 206 | 72 | Calculated Found | 64.64 64.50 | 6.08 6.15 | 12.06 11.98 |
| 72 417 | " | C₂₁H₂₂N₄O | 394.42 | 212 | 46 | Calculated Found | 63.94 63.74 | 5.62 5.66 | 14.21 14.19 |

(R = p-tolyl with H₂N–C(=O)– substituent)

Table II
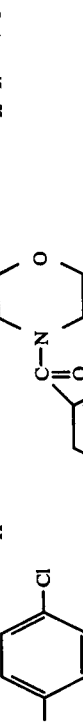
| Code No. | Ar | R₃ | R | Form | Epirical formula | Molecular weight | Melting point (°C) | Yield (%) | | Elementary analysis C | H | N |
|---|---|---|---|---|---|---|---|---|---|---|---|---|
| 76 0324 | 4-Cl-C₆H₄ | H | 3-(morpholinocarbonyl)phenyl | base | $C_{22}H_{21}ClN_4O_2$ | 408.88 | 200 | 65 | Cal. (%) Obt. (%) | 64.62 64.85 | 5.18 4.98 | 13.70 14.00 |
| 76 0325 | " | H | 2-(morpholinocarbonyl)phenyl | base | $C_{22}H_{21}ClN_4O_2$ | 408.88 | 254 | 70 | Cal. (%) Obt. (%) | 64.62 64.29 | 5.18 5.21 | 13.70 13.69 |
| 76 0326 | 2-Cl-C₆H₄ | H | 4-(morpholinocarbonyl)phenyl | chlor-hydrate | $C_{22}H_{22}Cl_2N_4O_2$ | 445.34 | >260 | 42 | Cal. (%) Obt. (%) | 59.33 59.02 | 4.98 4.93 | 12.58 12.27 |
| 76 0289 | C₆H₅ | CH₃ | 4-(morpholinocarbonyl)phenyl | base | $C_{23}H_{24}N_4O_2$ | 388.45 | 212 | 61 | Cal. (%) Obt. (%) | 71.11 71.40 | 6.23 6.52 | 14.42 14.21 |

The derivatives of formulas (I) and (II) were tested on laboratory animals and exhibited anti-anoxine properties according to the hypoxemia test described by Lauressergues et al (Therapie 26, 741, 1971).

The derivatives of formulas (I) and (II) were administered by intraperitoneal injection to batches of 10 male mice (T.O.P.S.-C.R.F.), 30 minutes before being placed in a glass desiccator where a barometric pressure of 190 mm Hg was created in 30 seconds. The survival time of the mice is estimated by the stopping of respiration. The significance of the effect in relation to that of non-treated type samples is calculated on the threshold $P = 0.05$ by the test $t$.

As examples, Table III below gives, for a certain number of derivatives, the first dose that provides significant protection by interperitoneal injection.

The protecting effect was shown with a dose at least equal (3.12 mg/kg/i.p.) to that of Vincamine taken as reference of activity (G. Perrault, M. Liutkus, R. Boulu and P. Rossignol-J. Pharmacol. (Paris) 1976, 7, (1), 27).

Table III also shows the results obtained by using the same method, but the administration of tested compounds was made orally and the test was effected an hour after administration.

Table III

| Compound tested | Hypobar hypoxemia test 1st dose of significant protection | |
|---|---|---|
| | Intraperitoneal injection (mg/kg) | Orally (mg/kg) |
| Derivatives of the invention | | |
| 72 256 | 0.78 | 12.5 |
| 72 276 | 1.56 | inactive at 25 |
| 72 741 | 3.12 | inactive at 25 |
| 72 608 | 3.12 | inactive at 25 |
| 72 621 | 3.12 | inactive at 25 |
| 72 417 | 3.12 | inactive at 25 |
| 72 536 | 0.78 | 12.5 |
| 75 0262 | 3.12 | inactive at 25 |
| 76 0324 | 3.12 | " |
| 76 0325 | 3.12 | " |
| 76 0326 | 3.12 | " |
| 76 0289 | 3.12 | " |
| Reference compound | | |
| Vincamine | 3.12 | 25 |

As can be seen from a comparison between the pharmacologically active doses mentioned above and the lethal doses below, the divergence between the doses is sufficient to permit the use of the derivatives for formulas (I) and (II) in therapeutics.

The derivatives of formula I have been tested on animals in the laboratory and have been shown to possess sedative, antiulcerous, antibronchooconstrictive and anticholinergic, diuretic, nalgesic and myorelaxant properties.

1. Sedative properties

The derivatives of formula I, administered by oral means to the mouse, reduce the number of explorations in the escape enclosure and in an actimeter having luminous beams and photoelectric cells.

By way of example, Code No. 72 536 effected a 75% diminution in the number of explorations in the escape enclosure, resulting from the administration of 100 mg/kg/p.o. of Code No. 72 536.

2. Antiulcerous properties

The derivatives of formula I, administered by oral means, reduce the extent of gastric ulcers provoked in a rat by typing of the pylorus (Shay ulcers)

Table IV indicates, by way of example, the results obtained by the administration of 50 mg/kg/i.d. of different derivatives of formula I.

Table IV

| Code No. of derivative tested | Percentage reduction of Shay ulcers % |
|---|---|
| 72 276 | 40 |
| 72 417 | 40 |
| 72 621 | 40 |

3. Antibronchoconstrictive and anticholinergic properties

Injected by intraduodenal means, the derivatives of formula I are capable of opposing the bronchoconstriction provoked in the guinea pig by the intravenous injection of acetylcholine and evaluated by the Konzett method.

By way of example, the following Table V lists the percentage inhibition of the bronchoconstriction following the intraperitoneal injection of 100 mg/kg of different derivatives of formula I.

Table V

| Code No. of derivative tested | Percentage inhibition of bronchoconstriction (%) |
|---|---|
| 72 276 | 50 |
| 72 608 | 65 |

4. Diuretic properties

The derivatives of formula I, administered by oral means to the mouse, simultaneously with a volume of 1 ml of an isotonic solution of sodium chloride per 25 g of the corporeal weight of the mouse, are capable of provoking an augmentation of the volume of urine emitted by reference to control animals, the volume being measured for 6 hours following administration.

By way of example the percentage augmentation of urinary elimination resulting from the administration of 25 mg/kg/p.o. of Code No. 72 416 caused 65% augmentation of urinary elimination.

5. Analgesic properties

The derivatives of formula I administered by oral means to the mouse, are capable of reducing the number of painful stretchings caused by the intraperitoneal injection of phenykbenzoquinone, acetic acid or bradykinine and can potentialise the analgesic action of dextromoramide in the Eddy test. By way of example, administration of 100 mg/kg/p.o. of Code No. 72 608 reduced by 55% the number of painful stretchings caused by intraperitoneal injection of phenylbenzoquinone.

6. Myorelaxant properties

The derivatives of formula I, preventively administered by oral means to the mouse, reduce the mortality caused by the sub-cutaneous injection of strychnine.

Thus, the derivative of Code No. 72608, administered in a dose of 100 mg/kg/p.o., permits a 50% protection against the lethality of styrchine.

Table VI

| Code No. of derivative tested | Toxicity Data Dose administered to the mouse (mg/kg/p.o.) | Percentage mortality (%) |
|---|---|---|
| 72 276 | 2 000 | 0 |
| 72 417 | 2 000 | 0 |
| 72 536 | 2 000 | 0 |

Table VI-continued

| Code No. of derivative tested | Toxicity Data Dose administered to the mouse (mg/kg/p.o.) | Percentage mortality (%) |
|---|---|---|
| 72 621 | 2 000 | ~30 |
| 72 608 | 1 600 | ~50 |
| 72 256 | 2 000 | 0 |
| 72 741 | 1 000 | 0 |
| 75 0262 | 1 000 | 0 |
| 76 0324 | 1 000 | 0 |
| 76 0325 | 1 000 | 0 |
| 76 0326 | 1 000 | 0 |
| 76 0289 | 1 000 | 0 |

The derivatives of formula (I) are useful in the treatment of gastro-duodenal ulcers, oedimas, anxiety, nervousness, contractions, and diverse originating pains.

They may be administered by oral means, in the form of tablets, gelules and dragees, containing 25 to 400 mg of active ingredient (1 to 6 times per day), or suspensions containing 0.2 to 5% of active ingredient (10 to 100 drops, 1 to 3 times per day), by parentereal means in the form of injectable ampoules containing 10 to 150 mg of active ingredient (1 to 3 times per day) and by rectal means in the form of suppositories containing 25 to 300 mg of active ingredient (1 to 3 times per day).

The derivatives of formulas (I) and (II) are effective in the treatment of cerebral deficiencies connected with an insufficiency of tissue oxygenation.

They will be administered orally in the form of pills, tablets and gelules containing 50 to 500 mg of the active ingredient (2 to 6 per day), in the form of a solution containing 0.5 to 5% of the active ingredient (20 to 60 drops — 2 to 6 times per day) and by parentereal injection in the form of injectable phials containing 50 to 500 mg of the active ingredient (1 to 3 per day).

Accordingly the present invention also relates to a therapeutic composition comprising a derivative of the formulas (I) and (II) together with a therapeutically acceptable carrier.

The embodiments of the invention in which an exclusive property or privilege is claimed are defined as follows:

1. A compound having the formula

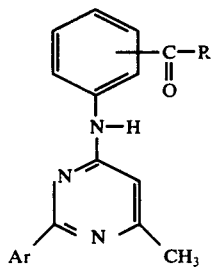

in which
  a. Ar is p-chlorophenyl and R is morpholino or piperidino, or
  b. Ar is o-chlorophenyl and R is morpholino, or
  c. Ar is m-fluorophenyl and R is piperidino, or
  d. Ar is 3,4-methylenedioxyphenyl and R is morpholino or amino, or
  e. Ar is 3,4,5-trimethoxyphenyl and R is morpholino or amino.

2. A compound as claimed in claim 1 in which Ar is p-chlorophenyl, R is morpholino and

is a para position.

3. A compound as claimed in claim 1 in which Ar is p-chlorophenyl, R is morpholino and

is in meta position.

4. A compound as claimed in claim 1 in which Ar is p-chlorophenyl, R is morpholino and

is in ortho position.

5. A compound as claimed in claim 1 in which Ar is p-chlorophenyl, R is piperidino and

is in para position.

6. A compound as claimed in claim 1 in which Ar is m-fluorophenyl, R is piperidino and

is in para position.

7. A compound as claimed in claim 1 in which Ar is 3,4-methylenedioxyphenyl, R is morpholino and

is in para position.

8. A compound as claimed in claim 1 in which Ar is 3,4-methylenedioxyphenyl, R is —NH₂ and

is in ortho position.

9. A compound as claimed in claim 1 in which Ar is 3,4,5-trimethoxyphenyl, R is morpholino and

is in para position.

10. A compound as claimed in claim 1 in which Ar is 3,4,5-trimethoxyphenyl, R is —NH₂ and

is in para position.

11. A compound as claimed in claim 1 in which Ar is o-chlorophenyl, R is morpholino and
is in para position.
12. A compound having the formula
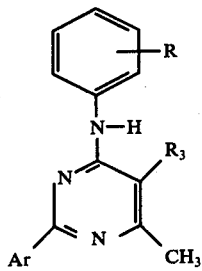
in which Ar is phenyl or phenyl substituted by a halogen, R is
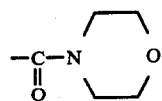
and $R_3$ is hydrogen or methyl.
13. A compound as claimed in claim 12 in which Ar is phenyl, R is
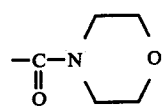
in para position and $R_3$ is methyl
* * * * *